United States Patent [19]
Senaratne et al.

[11] Patent Number: 5,241,085
[45] Date of Patent: Aug. 31, 1993

[54] PREPARATION OF CYCLIC ETHERS

[75] Inventors: K. Pushpananda A. Senaratne; Patrick S. Bynum; Kenneth C. Lilje; Edward F. Zaweski, all of Baton Rouge, La.

[73] Assignee: Ethyl Corporation, Richmond, Va.

[21] Appl. No.: 980,067

[22] Filed: Nov. 23, 1992

Related U.S. Application Data

[62] Division of Ser. No. 769,644, Oct. 2, 1991, Pat. No. 5,196,552.

[51] Int. Cl.$^5$ .................. C07D 309/18; C07D 311/94; C07D 307/28
[52] U.S. Cl. .................. 549/396; 549/356; 549/507
[58] Field of Search .................. 549/396, 356, 507

Primary Examiner—Nicky Chan
Attorney, Agent, or Firm—David M. Bunnell

[57] ABSTRACT

Cyclic ethers are prepared by reacting an unsaturated olefin oligomer derived from an alpha-olefin monomer containing from about 6 to 20 carbon atoms with an aldehyde in the presence of an acid catalyst.

10 Claims, No Drawings

PREPARATION OF CYCLIC ETHERS

This application is a division of application Ser. No. 07/769,644, filed Oct. 2, 1991, now U.S. Pat. No. 5,196,552.

This invention relates generally to functionalized polyalphaolefin oligomers useful in lubricant applications and more particularly to unsaturated polyalphaolefin oligomers which have been reacted with aldehydes to form cyclic ethers.

Alpha-olefin oligomers (PAO's) derived from $C_6$ or higher alpha-olefin monomer and their use as functional fluids and synthetic lubricants are well known. Such oligomers are usually hydrogenated to improve their oxidation resistance and are known for their superior properties of long-life, low volatility, low pour points and high viscosity indexes which make them a premier basestock for state-of-the-art lubricants and hydraulic fluids. A problem associated with such basestocks is that polar lubricant additives are generally less soluble in PAO's than in mineral oils. Therefore, PAO's have been reacted with compounds which contain polar groups, such as phenols, in order to improve their compatibility with polar additives. According to the Prins reaction, alkenes react with aldehydes such as formaldehyde in the presence of acid catalysts to produce, depending upon the reaction conditions, unsaturated alcohols, 1,3-glycols and/or dioxanes. Surprisingly, we have found that when unsaturated PAO's are reacted with aldehydes the adducts are mono- and/or polycyclic ethers. These cyclic ethers can abe used as lubricant additives and especially as additives in PAO based lubricants.

In accordance with this invention there are provided a mixture of cyclic ethers prepared by the process comprising reacting an unsaturated olefin oligomer derived from an alpha-olefin monomer containing from about 6 to 20 carbon atoms with an aldehyde in the presence of an acid catalyst.

Also provided is a process for preparing a mixture of cyclic ethers comprising reacting an unsaturated olefin oligomer derived from an alpha-olefin monomer containing from about 6 to 20 carbon atoms with an aldehyde in the presence of an acid catalyst.

The preparation of alpha-olefin oligomers is well known. For example, U.S. Pat. No. 3,113,167 describes an alpha-olefin oligomer process using a titanium halide and an aluminum compound as the oligomerization catalyst.

Other suitable catalysts for making alpha-olefin oligomers are Friedel-Crafts catalysts such as boron trifluoride ($BF_3$) as disclosed in U.S. Pat. No. 3,149,176. Optimum lubricant properties are obtained starting with 1-decene although mixtures of alpha-olefins have been used cf. U.S. Pat. No. 3,330,883. Pure $BF_3$ is not an effective oligomerization catalyst. A small amount of polar compound is necessary as a promoter. U.S. Pat. No. 3,382,291 describes the use of alcohol promoters such as decanol. Alcohols containing about 1-8 carbon atoms such as methanol, ethanol, isopropanol, n-propanol, n-butanol, isobutanol, n-hexanol and n-octanol can also be used. A preferred promoter is n-butanol. Other promoters include, for example, mordenite (hydrogen form), water, phosphoric acid, fatty acids (e.g. valeric acid), aldehydes, ketones, organic esters, ethers, polyhydric alcohols, silica gel and the like.

The amount of promoter is an amount that causes the $BF_3$ to act as an oligomerization catalyst. A useful range is about 0. to 2.0 weight percent of the alpha-olefin.

Methods of conducting a $BF_3$ catalyzed oligomerization process are well-known. In one mode, $BF_3$ is merely bubbled through the alpha-olefin reaction mixture containing a promoter during the oligomerization. Generally, the process is conducted under $BF_3$ pressure. A useful pressure is about 1-100 psig and especially 5-50 psig.

Alpha-olefins most useful in preparing synthetic lubricant oils are mainly linear terminal olefins containing about 8-12 carbon atoms such as 1-octene, 1-decene, 1-dodecene and the like including mixtures thereof. The most preferred alpha-olefin is 1-decene or an olefin mixture containing mainly, for example at least 75 weight percent 1-decene.

Generally, reaction temperatures are about 20°-50° C. and especially about 25°-40° C.

The oligomer products are mixtures which include varying amounts of dimer, trimer, tetramer, pentamer and higher oligomers of the monomer, depending upon the particular alpha-olefin, catalyst and reaction conditions. The products are unsaturated and usually have viscosities ranging from about 2 to 100 cSt and especially 2 to 15 cSt at 100° C.

Preferred oligomer products for use in preparing the cyclic ethers of the invention are dimers of 1-decene ($C_{20}H_{40}$).

Preferred aldehydes for use in the invention are the aliphatic aldehydes, formaldehyde, (including paraformaldehyde) and acetaldehyde which provide cyclic aliphatic ethers.

Effective acid catalysts for the process include Lewis acids such as, for example, zinc chloride, stannic chloride, $TiCl_4$, $BF_3$ etherate, alkyl aluminum halides (e.g. methyl aluminum dichloride and dimethyl aluminum chloride) and the like. Sulfuric acid (50%) and Amberlist 15 did not provide any yield of product under the conditions tried.

The reaction can be carried out neat but yields are improved by the use of an organic solvent and especially a halogenated organic compound. Examples of suitable solvents include methylene chloride, dichloroethane, acetic acid, hexane, heptane, xylene, ether, and the like, including mixtures thereof.

Reactant to catalyst ratios can vary and are selected to provide optimum yields for any particular olefin, aldehyde and catalyst combination. Molar ratios of alpha-olefin to aldehyde to catalyst can range, for example, from about 1:0.5:0.05 to about 1:4:2.

The process can be carried out at ambient temperatures but higher or lower temperatures can also be used, for example from about 0° C. to 90° C. When used, the amount of solvent is not particularly critical and generally ranges from about 60 to 85 weight percent of the total amount of reaction mixture.

The reaction mixture is washed to remove the catalyst and excess aldehyde, dried and then concentrated to remove the solvent such as by vacuum evaporation.

The cyclic ethers derived from olefin oligomer I are believed to contain both five and six membered rings.

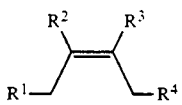

where $R^1$, $R^2$, and $R^3$ are $C_1$ to about $C_{50}$ alkyl and $R^4$ is $C_1$ to $C_4$ alkyl or hydrogen.

Cyclic ether products include those having the following structures II, III and IV:

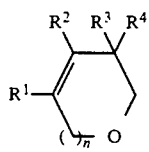

where n = 1 or 0

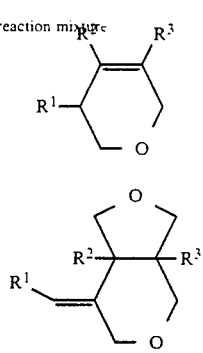

Structures III and IV are derived from I when $R^4$ is hydrogen and structure II where $R^4$ is alkyl. Because the starting PAO's are complex mixtures of isomers, the cyclic ether products are also mixtures.

The ethers can be hydrogenated to form saturated compositions by standard hydrogenation procedures using, for example, platinum, nickel or palladium catalysts. Such hydrogenation provides lubricating oils having improved oxidation resistance compared to the unsaturated compositions.

The invention is further illustrated by, but is not intended to be limited to, the following examples.

EXAMPLE 1

Approximately 40 ml of anhydrous dichloroethane and 5.00 grams (17.8 mmol) of $C_{20}H_{40}$, which is the product of a $BF_3$ promotor catalyzed dimerization of 1-decene, were added to a 100-ml flask with a nitrogen purge. With stirring, 2.00 grams of paraformaldehyde (66.7 mmol of formaldehyde) were added to the solution. Finally, $BF_3$ was bubbled through the solution for one minute, and the solution was left to stir at room temperature for 18 hours. The solution was washed with ethyl ether and dilute sodium bicarbonate. The aqueous layer was removed, and the solution was washed one final time with water. The two layers were separated, the organic layer was dried over magnesium sulfate and the solution was then concentrated using a rotoevaporator. Gas chromatography shows the yield of products to be 96%. Mass spectrometry indicates that the two products have molecular weights of 322 g/mol monocyclic ether (38% yield by GC) and 364 g/mol dicyclic ether (58% yield by GC).

EXAMPLES 2-11

The procedure of Example 1 was generally followed using the $C_{20}H_{40}$ olefin except using different catalysts, solvents, and reaction times and temperatures. The process parameters and results are reported in Table I.

TABLE I

| Example | Catalyst | Solvent | Aldehyde | Mole Ratio Olefin/Aldehyde/Catalyst | Temp. | Time Hrs | Yield % | Mono[1] | Di[2] | Unk.[3] |
| --- | --- | --- | --- | --- | --- | --- | --- | --- | --- | --- |
| 2 | $SnCl_4$ | Methyl Chloride | Formaldehyde | 1:3.7:0.05 | RT | 18 | 31 | 31 | <1 | |
| 3 | $SnCl_4$ | Dichloroethane | Formaldehyde | 1:3.7:0.05 | Reflux | 4 | 81 | 47 | 34 | |
| 4 | $BF_3$ | Methylene Chloride | Formaldehyde | 1:1.1:excess | RT | 18 | 64 | 64 | <1 | |
| 5 | $BF_3Et_2O$ | Dichloroethane | Formaldehyde | 1:1.1:0.05 | RT | 4 | 32 | 32 | <1 | |
| 6 | $BF_3Et_2O$ | Dichloroethane | Formaldehyde | 1:1.1:0.05 | Reflux | 18 | 60 | 60 | <1 | |
| 7 | $BF_3Et_2O$ | Hexane | Formaldehyde | 1:1.1:0.05 | RT | 18 | 32 | 24 | 6 | 2 |
| 8 | $BF_3Et_2O$ | Methylene Chloride | Formaldehyde | 1:3.7[4]:0.05 | RT | 56 | 47 | 24 | 4 | 19 |
| 9 | $BF_3$ | DCE/Acetic Acid | Formaldehyde | 1:1.1:excess | RT | 18 | 71 | 71 | 0 | |
| 10 | $BF_3$ | DCE/Acetic Acid | Formaldehyde | 1:1.1:excess | RT | 42 | 80 | 38 | 0 | 41[5] |
| 11 | $BF_3$ | Acetic Acid | Formaldehyde | 1:1.1:excess | RT | 18 | 55 | 49 | 6 | |
| 12 | $BF_3$ | Dichloroethane | Acetaldehyde | 1:1.1:excess | RT | 18 | 54 | 50 | <1 | |

[1] Monocyclic ether
[2] Dicyclic ether
[3] Unidentified
[4] Bubbled into the reaction mixture
[5] Probably polymer The solubility of a sulfurized isobutylene (5 wt. percent) in a 40 cSt (100° C.) polyalphaolefin base oil was improved by about 37%, as measured by a decrease in turbidity from 94.6% to 59.8%, by adding 5 wt. percent of the cyclic ether product mixture from Example 1 to the base oil.

What is claimed is:

1. A process for preparing a mixture of cyclic ethers said process comprising reacting a mixture of an oligomer derived from an alpha-olefin, monomer containing from about 6 to 20 carbon atoms and an aliphatic aldehyde in the presence of an acid catalyst.

2. The process of claim 1 wherein said catalyst is a Lewis acid.

3. The process of claim 1 wherein the mixture includes an organic solvent.

4. The process of claim 3 wherein the oligomer is derived from 1-decene, the catalyst comprises $BF_3$, the organic solvent is a halogenated organic compound, the aldehyde is a formaldehyde or acetaldehyde and the ratio of alpha-olefin to aldehyde to catalyst ranges from about 1:0.5:0.05 to 1:4:2.

5. The process of claim 4 wherein the oligomer is 1-decene dimer, the catalyst is selected from $BF_3$, $BF_3$-$Et_2O$ and $SnCl_4$, and the solvent is selected from methylene chloride and dichloroethane.

6. The process of claim 1 wherein said oligomer is derived from the Friedel-Crafts catalyzed oligomerization of the alpha-olefin.

7. The process of claim 4 wherein said oligomer is derived from the Friedel-Crafts catalyzed oligomerization of the alpha-olefin.

8. The process of claim 7 wherein the Friedel-Crafts catalyst is a $BF_3$-promotor complex.

9. The process of claim 1 including hydrogenating said mixture.

10. The process of claim 4 including hydrogenating said mixture.

* * * * *